US00PP14628P29

(12) United States Plant Patent
Danziger

(10) Patent No.: US PP14,628 P2
(45) Date of Patent: Mar. 23, 2004

(54) IMPATIENS PLANT NAMED 'DANCHEPURJOY'

(50) Latin Name: *Impatiens walleriana*
Varietal Denomination: Danchepurjoy

(75) Inventor: Gabriel Danziger, Nir-Zvi (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 10/230,134

(22) Filed: Aug. 29, 2002

(51) Int. Cl.[7] ..... A01H 5/00
(52) U.S. Cl. ..... Plt./317
(58) Field of Search ..... Plt./317

*Primary Examiner*—Bruce R. Campell
*Assistant Examiner*—June Hwu
(74) *Attorney, Agent, or Firm*—Foley & Lardner

(57) ABSTRACT

A new and distinct Impatiens plant named 'Danchepurjoy' characterized by having compact growth habit; small flowers; small, green leaves; and purple flowers.

1 Drawing Sheet

Latin name of the genus and species of the plant claimed: *Impatiens walleriana.*
Variety denomination: Danchepurjoy.

BACKGROUND OF THE INVENTION

The present invention relates to a new and distinct cultivar of Impatiens plant, botanically known as *Impatiens walleriana* hereinafter referred to by the cultivar name 'Danchepurjoy'.

The new cultivar originated from a cross made in a controlled breeding program in Moshav Mishmar Hashiva, Israel. The female parent is designated FRB-201 (unpatented, proprietary cultivar). The male parent is designated BGA-202 (unpatented, proprietary cultivar). 'Danchepurjoy' was discovered and selected by the inventor, Gabriel Danziger, as a flowering plant within the progeny of the stated cross in a controlled environment in Moshav Mishmar Hashiva, Israel.

Asexual reproduction of the new cultivar by leaf cuttings was first performed in April, 2000 in Moshav Mishmar Hashiva, Israel and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'Danchepurjoy' which in combination distinguish this Impatiens as a new and distinct cultivar:

1. compact growth habit;
2. small flowers;
3. small, green leaves;
4. purple flowers.

'Danchepurjoy' has not been observed under all possible environmental conditions. The phenotype of the new cultivar may vary significantly with variations in environment such as temperature, light intensity, and daylength without any change in the genotype of the plant.

Of the many commercial cultivars known to the present inventor, the most similar in comparison to 'Danchepurjoy' is the Impatiens variety 'Fify Violet' (U.S. Plant Pat. No. 11,557), commercially known as 'Firefly Violet'.

TABLE 1

| | 'Danchepurjoy' | 'Firefly Violet' |
|---|---|---|
| Petal Color | RHS 71C (upper surface); RHS 72C (lower surface) | RHS 74A (upper surface); RHS 74B (lower surface) |
| Leaf Color-upper surface | RHS 137D | RHS 147A |
| Flower Size | 1.9 cm | 2 cm |

BRIEF DESCRIPTION OF THE DRAWING

The accompanying photographic drawings illustrate the overall appearance of the new Impatiens showing the colors as true as is reasonably possible with colored reproductions of this type. The drawing shows a whole plant side-view of a flowering potted 'Danchepurjoy' plant.

DETAILED BOTANICAL DESCRIPTION

The following observations, measurements and values describe the new cultivar as grown in Moshav Mishmar Hashiva, Israel under conditions which closely approximate those generally used in commercial practice. The plant is grown in a greenhouse under the typical Israeli weather conditions (Winter night time temperature 18° C., winter day time temperature 20–25° C.; summer night time temperature 25° C., summer day time temperature 30° C.). Fertilization: N: P: K=5:3:8, N=100 ppm.

Color references are made to The Royal Horticultural Society Colour Chart (R.H.S.), except where general colors of ordinary significance are used. Color values were taken under daylight conditions at approximately noon. The age of the plant described is 13 weeks from planting. The plant was asexually reproduced by leaf cuttings.

Plant:

*General appearance and form.*—Height: Approximately 15 cm. Plant spread: Compact, 30 cm. Lateral branches: Length 14 cm; internode length 2.5 cm; diameter 0.5 cm; branch color RHS 147C anthocyanin color RHS 183B. Flowering Response: Flowers at any day length. Flowering Season: Year round as grown in a greenhouse with winter night time temperature of 18° C., winter day time temperature of 20–25° C.; summer night time temperature of 25° C., and summer day time temperature of 30° C. Winter Hardiness: Resistance to 10° C. Lastingness of the Individual Bloom: Approximately 15 days. Root Description: Adventitious roots from cutting base. Time to initiate roots: 10 days. Time to produce a rooted cutting or liner: 17 days. Growth and branching habit: Compact growth habit, strong branching. Crop time: 10 weeks after planting in a 10–12 cm pot. Fragrance: None.

Foliage:

*Leaf shape.*—Elliptic.

*Apex.*—Acuminate.

*Base.*—*Acute.*

*Length.*—Approximately 3 cm.

*Width.*—Approximately 2 cm.

*Margin.*—Shallowly serrate.

*Texture.*—Smooth.

*Color of upper surface.*—Mature leaf: RHS 137A. Immature leaf: RHS 137C.

*Color of lower surface.*—Mature leaf: RHS 139D. Immature leaf: RHS 139D.

*Venation.*—Pinnate.

*Petiole.*—Length: 1.5 cm. Diameter: 2 mm. Color: RHS 138D.

Inflorescence:

*Flower type and habit.*—Single flower, day neutral.

*Overall shape.*—Irregular — 5 petaled.

*Flower size.*—Diameter 1.9 cm.

*Average number of flowers per lateral branch.*—Approximately 15.

*Petals.*—Petal Number: 5. Petal Shape: Spatulate; apex obtuse; base acute; margin entire. Texture: Smooth. Petal size: Length approximately 1.3 cm; width approximately 0.8 cm. Petal Color: Upper surface: Purple RHS 71C. Lower surface: Purple RHS 71C.

*Sepals.*—Number: 2. Shape: Elliptic. Length: 2 mm. Width: 1 mm. Apex: Acute. Margin: Entire. Color: Yellow-green, RHS 145C.

*Stem.*—Average length: 15 cm. Average diameter: 1 cm.

*Color.*—Green RHS 147C. Internode length: 2 cm.

*Spur.*—Length 1.5 cm; color red RHS 50C.

*Bud.*—Rate of opening: From the emergence of color until anthesis: 2 days. Color: RHS 149D. Shape: Conical Length: 0.7 cm. Diameter: 0.5 cm.

*Peduncles.*—Length about 1.5 cm; slightly upward angle; strength is stable; smooth surface texture; color yellow-green, RHS 145B.

Reproductive organs:

*Stamen.*—Number: 5. Size: 2 mm. Color: Purple RHS 77C.

*Seeds.*—Width: 1 mm. Length: 1 mm. Shape: Lanceolate. Color: Brown RHS 165A.

*Fruit.*—Size: 0.5 mm. Color: Green RHS 144A.

*Anthers.*—Color: RHS 63B.

*Pollen.*—None. Pistil: Size: 2 mm. Stigma: Color: Green RHS 144B. Size: 2 mm. Ovary: Color: Green RHS 144B.

Disease resistance: No sensitivity to disease was observed under regular growing conditions.

I claim:

1. A new and distinct Impatiens plant named 'Danchepurjoy', substantially as illustrated and described herein.

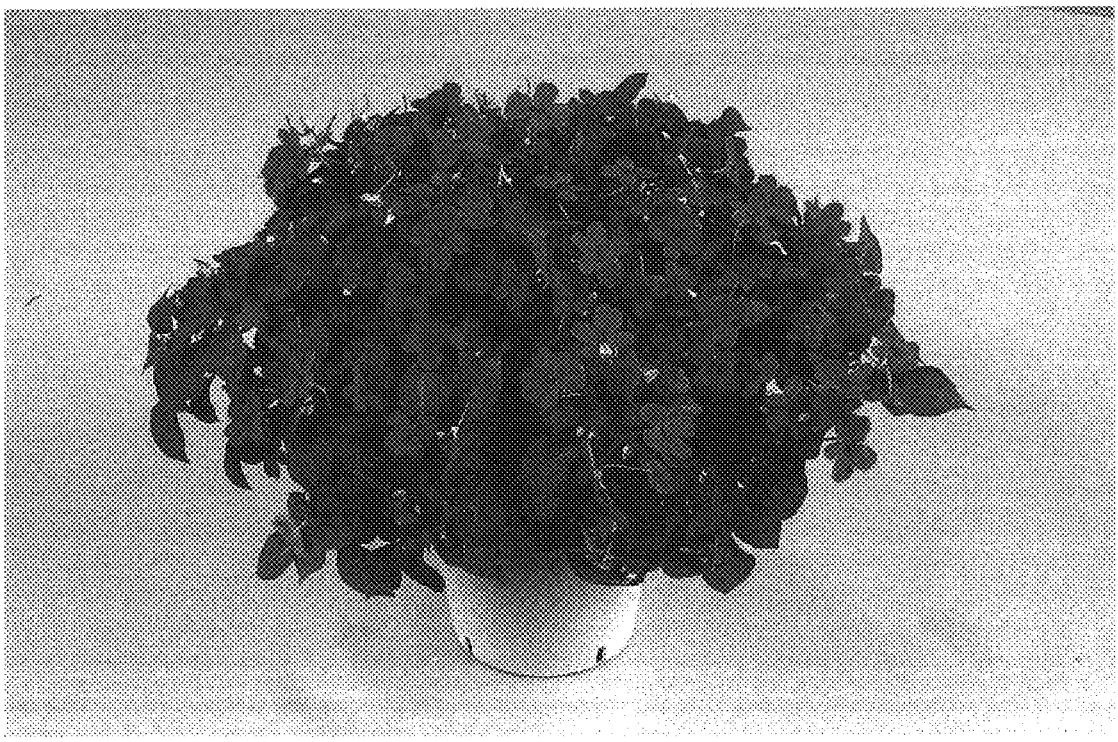

* * * * *